US00RE37274E

(19) United States
(12) Reissued Patent
Gardner

(10) Patent Number: US RE37,274 E
(45) Date of Reissued Patent: Jul. 10, 2001

(54) METHOD FOR NUTRITIONAL OXYGENATION OF THE SKIN

(76) Inventor: John P. Gardner, 1025 S. Ouray St., Aurora, CO (US) 80017

(21) Appl. No.: 09/078,831

(22) Filed: May 14, 1998

Related U.S. Patent Documents

Reissue of:
(64) Patent No.: 5,516,517
Issued: May 14, 1996
Appl. No.: 08/236,400
Filed: May 2, 1994

(51) Int. Cl.[7] ..... A61K 7/48
(52) U.S. Cl. ..... 424/401; 424/94.1; 424/195.1; 514/844
(58) Field of Search ..... 424/401, 94.1, 424/195.1; 514/844

(56) References Cited

U.S. PATENT DOCUMENTS

| | | | |
|---|---|---|---|
| 123,714 | 2/1872 | Martin . | |
| 3,810,996 | 5/1974 | Sutliff et al. | 424/364 |
| 4,743,442 | 5/1988 | Raaf et al. | 424/47 |
| 4,751,075 | 6/1988 | Chernowsky et al. | 424/83 |
| 4,810,496 | 3/1989 | Jensen | 424/127 |
| 4,911,925 | 3/1990 | Shatkina et al. | 424/401 |
| 4,992,476 | 2/1991 | Geria | 514/782 |
| 5,063,062 | 11/1991 | Greenspan et al. | 424/443 |
| 5,080,901 | 1/1992 | Hangay et al. | 424/195.1 |
| 5,162,377 | 11/1992 | Kakoki et al. | 514/772 |
| 5,227,161 | 7/1993 | Kessler | 424/94.4 |
| 5,229,130 | 7/1993 | Sharma et al. | 424/449 |
| 5,242,952 | 9/1993 | Tritsarolis | 514/783 |
| 5,254,331 | 10/1993 | Mausner | 424/59 |
| 5,516,517 | 5/1996 | Gardner | 424/401 |

FOREIGN PATENT DOCUMENTS

| | | |
|---|---|---|
| 647145A | 1/1985 | (CH) . |
| 484139 | 10/1929 | (DE) . |

*Primary Examiner*—Jyothsna Venkat

(57) ABSTRACT

A skin treatment process designed to reduce the aging process of the skin and to cause the skin to become a semi-permeable membrane. The steps include exfoliation, cleansing, hydration, and oxygenation. By placing solutions ranging from a pH substantially in the range of 4.5 to 8.8 on the skin in a predetermined order, the skin will be able to accept a oxygenated mist of moisturized nutrients on a pore-by-pore basis.

16 Claims, No Drawings

METHOD FOR NUTRITIONAL OXYGENATION OF THE SKIN

Matter enclosed in heavy brackets [ ] appears in the original patent but forms no part of this reissue specification; matter printed in italics indicates the additions made by reissue.

BACKGROUND OF THE INVENTION

This invention relates to a process and treating solution for the nutritional oxygenation of the skin via the steps of exfoliation, cleansing, hydration, and oxygenation. The steps of the process are performed by using various solutions that are adjusted to specific pH levels to condition the skin and allow the skin to receive each level of nutrients on a pore-by-pore basis.

Oxygen is a critical element in the maintenance of healthy skin, just as it is crucial to the normal functioning of our bodies in general. The use of oxygen to increase the healing of skin wounds caused by disease or injury is well documented by medical researchers, clinicians, and physicians around the world. The majority of this documentation is found in textbooks and literature detailing hyperbaric oxygenation as well as oxygenated limb pressure units. So far, however, there has been a limited number of programs established that are clinically advanced enough to use oxygen cosmetic skin treatments.

The proper use of oxygen is even more important considering that there are more than ninety harmful contaminants dumped into the air every day that are detrimental to the skin. Under certain conditions, skin is porous and will allow the passage of certain molecular contaminants, many of which are lyophilic and can remain on subcutaneous fat for a considerable length of time. Medical authorities have documented alarming increases in virtually every type of skin cancer known since the proliferation of many of these toxic airborne contaminants.

Traditional practices of skin care in the prior art have been very limited. The emphasis has been placed on cleansing and cosmetics, rather than prevention and treatment. As a result, the prior art provided only short-term relief with no lasting benefit to the skin. In fact, many methods currently employed are damaging to facial skin and are thus undesirable.

Specifically, the problem of moisturizing the skin with the currently available creams, oils and lotions is that many of the ingredients used therein clog the pores and may cause infection to occur. Also, complete and effective moisturization of the skin is not entirely possible due to the size and structure of the molecules in the lotions, oils and creams.

There have only been a few programs established that are clinically advanced enough to use oxygen via a cosmetic means. Cosmetic oxygenation of normal skin serves the purpose of increasing topical nutrition and acids in the prevention or retardation of the degenerative process. Cosmetic oxygenation may also be successfully used to reduce the negative effects of skin degeneration caused by atmospheric contaminations.

The fundamental principle underlying the present invention is to deter the negative impact of minute particles that may become embedded in the skin and subsequently destroy the skin cells. The process of the present invention is designed to cause the skin to become a semi-permeable membrane by the topical application of various solutions that are pH adjusted within a predetermined range. By placing these pH adjusted solutions on the skin at various intervals, and massaging vitamins and minerals directly onto the skin's surface, the skin will be encouraged to respond topically and accept an oxygenated mist of moisturized nutrients into the skin.

It is therefore a primary objective of this invention to provide a skin care treatment that will provide a strong nutrient base for the care of the skin that will include the use of the oxygen molecule.

A further objective of the present invention is to add an abundance of moisturized nutrients composed of vitamins, minerals, enzymes, amino acids, and oxygen into tile skin.

It is a further objective of the present invention to effect a greater deposition of submicronic nutrients to the skin cells on a pore-by-pore basis.

A still further objective of the present invention is to reduce the intrinsic and extrinsic aging process by increasing the tensillary strength of the underlying skin cells.

The method and manner of accomplishing each of the above objectives as well as others will become apparent from the detailed description of the invention which follows.

BRIEF SUMMARY OF THE INVENTION

A process of exfoliation, cleansing, hydration, and oxygenation is used to provide nutritional oxygenation of the skin. To begin, a two step exfoliation process consists of first using an alkalinic solution to break down skin cells immediately on contact, then using a slightly acidic solution to help neutralize the alkalinic solution and calm the skin. Second, the cleansing step uses a bacteriostatic agent to tone the skin and to make the skin a "sterile" environment. Third, the hydration step uses applied vitamins and minerals to create a semi-permeable keratinized layer which adapts the skin to receive higher amounts of nutrients. Finally, the oxygenation step saturates each pore with oxygen so that the skin will absorb a select amount of molecular nutrients on a pore-by-pore basis.

DETAILED DESCRIPTION OF THE INVENTION

This invention is a process consisting of the steps of exfoliating the skin, cleansing the skin, hydrating the skin, and oxygenating the treated area. In general, exfoliation is accomplished by first applying an alkalinic solution to the facial area, followed by an application of an acidic solution as a neutralizer. Cleansing of the skin is accomplished by applying a solution containing a bacteriostatic agent. To hydrate the skin, select amounts of vitamins A and E and minerals are applied to the skin. Finally, the skin is oxygenated with a nebulizer thereby providing nutrients to the skin on a pore-by-pore basis.

I. Exfoliation

The first part of this process utilizes an Exfoliant I solution. It is titrated to be an alkalinic solution with a pH substantially in the range of 8.2 to 8.5. The method of operation is purely enzymatic (and enhancement ) with base line surfactants. The solution is a combination of mild enzymatic cleansing agents and an electrolyte soap. Enzymes useful include protolific enzymes such as papain, 0.2–0.5% hydrolytic enzymes such as bromelain 0.3–0.7% and citrus fruit extracts which contain other digestive enzymes in an amount of 0.2 –0.5%. These enzymes are traditionally used in meat tenderizing. Next the solution includes an electrolytic cleansing agent such as potassium chloride soap in an amount of 28–34%. Various moisturizers such as aloe vera may be added in amounts of 8–12%.

Optionally the solution may include an emulsion stabilizer oil-base substance such as almond oil.

Finally the pH of the solution is adjusted by addition of a saline solution to 8.2 to 8.5. A solution according to this step was prepared and is listed below. The ingredient, its purpose, is contemplated percentage, and is approximate useful range by percentage by weight is as follows:

| Ingredient | Purpose | Percentage (by weight) | Allowable Range |
|---|---|---|---|
| Almond Oil | Stabilizer | 20% | 20–22% |
| Papain (enzymes extracted from papaya) | Digestive Enzymes | 0.4% | 0.2–0.5% |
| Pottassium Chloride Soap | Electrolyte | 30% | 28–34% |
| Aloe Vera | Plant Extract | 10% | 8–12% |
| Bromelain | Hydrolytic Enzyme | 0.5% | 0.3–0.7% |
| Grapfruit | Digestive | 0.1% | 0.2–0.5% |
| pH adjusted Isotonic Saline (.9% NA) | | 2% | 1–3% |
| Sterile Distilled $H_2O$ or Demineralized | | 35% | 32–37% |

This solution is then applied to the face to condition the skin, in preparation for the next acidic application. In the preferred embodiment, the solution is massaged into the skin to enhance absorption.

An example procedure for using the Exfoliant I solution is as follows: First, shake the Exfoliant I solution well. Place 1–2cc's of the Exfoliant I solution on a clean exfoliant pad and begin to apply to the facial area of the user from the neck up. Eye makeup, such as mascara, may be removed from the eyes with the soaked pad. It is important to be careful not to rub the solution into the eyes. Some users may require a second application of the Exfoliant I if makeup cannot be completely removed. Second, 1–2cc's of the Exfoliant I solution are massaged into the skin with slow, controlled strokes. As the solution is worked into the skin, it will begin to loosen and slip on the skin's surface. This step is for exfoliation, although lymphatic drainage may be done at this time.

The surface active agents of the Exfoliant I solution will have completed conditioning the skin after only 1–2 minutes.

The second part of the exfoliation process utilizes the Exfoliant II solution. It is tritrated to be a more acidic solution having a pH substantially in the range of 4.3 to 4.5. Its purpose is to help neutralize the Exfoliant I and calm the skin to continue enhancement effect.

The second solution comprises a mixture of calming agents such as allantoin, comfrey, and chamomile in stabilizers such as ginger or aloe vera. The mixture is adjusted to a pH in the range of 4.3 to 4.5. Their solution is similarly applied to the skin, and any facial debris is removed preferably by a cool towel. A preferred embodiment of the Exfoliant II solution was prepared according to the invention. It contains the following:

| Ingredient | Purpose | Percentage (by weight) | Allowable Range |
|---|---|---|---|
| Aloe Vera | Stabilizer | 7% | 5–9% |
| Balm Mint Extract | pH Adjuster | 0.2% | 0.1–0.3% |
| Allansoin | Calming, pH Adjuster | 0.4% | 0.2–0.5% |

-continued

| Ingredient | Purpose | Percentage (by weight) | Allowable Range |
|---|---|---|---|
| Hawaiian Ginger | Stabilizer | 0.3% | 0.2–0.4% |
| Chamomile | Calming | 0.8% | 0.7–0.9% |
| Sterile Distilled Water or Demineralized Water | | 89% | 87–90% |
| Hypotonic Saline | | | 2% |

A sample procedure for using the Exfoliant II solution is as follows: First, place 1 2cc's of the Exfoliant II solution onto two cotton pads and massage the solution slowly, with a small amount of pressure, onto the facial skin area to be treated. Lathering should occur. However, some skin will absorb the product more readily and lathering may be negligible.

Second, place a cool towel, soaked in distilled or demineralized water, around the facial area and begin slowly and softly wiping off the topical debris, making sure the towel is not too wet. Repeat until as much residue has been removed from the skin as possible. The cool towel will constrict the muscles and force sub strata toxins to the surface, and extractions may be done at this time.

II. Cleansing

Next, the cleansing step is accomplished by means of a bacteriostatic agent, such as ergocalciferal. This step may also include calming and toning and salve agents as well. The action of the cleansing solution is to perform primarily as a bacteriostatic agent against S. aureus bacteria on the skin without harming much of the beneficial E. coli. The balance of certain bacteria on the skin keeps in check certain forms of ache. In the preferred embodiment of the invention, the cleansing solution may be prepared as follows:

| Ingredient | Purpose | Percentage (by weight) | Allowable Range |
|---|---|---|---|
| Wintergreen, Spearmint and Pepermint Oil | | 0.4% | 0.2–0.5% |
| Citronella | Toning Agent | 0.4% | 0.2–0.6% |
| Ergocalciferol | Bacteriostatic Agent | 0.9% | 0.7–1.0% |
| Balm Mint Oil Extract | | 0.2% | 0.1–0.3% |
| Sterile Distilled Water | | 94% | 97–97% |
| or Demineralized | | 3.7% | 2.0–4.0% |
| Hypotonic Saline | | | |

The procedure for using the cleansing solution is as follows: First, place 2–3cc's of the cleansing solution on a clean cotton pad. Rub smoothly and continually over the surface of the skin from the neck area up.

III. Hydration

This step is often termed "Osmotic Hydration" and involves a process of molecular dispersion to enhance the stratum corneum. A selectively semi-permeable keratinized layer is created that will allow the skin to receive a higher level of nutrients because of sub-micronic, pore-by-pore deposition. Vitamins A an E and liquid minerals are strategically placed on the skin for absorption.

An example of the molecular dispersing ingredients are shown in the following example:

| Ingredient | Amount |
|---|---|
| Mycelated d-Alpha Tocopherol-Higher potency and action gtts | 150 IU/3 |
| Mycelated Retinol Palmitate-Higher potency and action gtts | 75 IU/3 |
| Simmondsia Cheninstis (Pure Jojoba) | 2 gtts |
| Liquid Minerals (Trace Sea Derived) | 0.4 gtts |
| Hygroscopic Enzymes (NaPCA) | 0.03 gtts |
| Sterile Distilled Water | 30 gtts |
| Hypotonic Saline | 5 gtts |

The procedure for using the vitamins and minerals is as follows: First, taking 2–3 drops of liquid minerals, apply to the lips and ear lobes. Second, strategically place 3 drops of mycelated retinol palmitate onto the neck, chin and forehead. Third, place 2 drops of the mycelated d-alpha tocopherol on both cheeks of the user's face and 4 drops of simmondsia cheninsis into the applicant's palm. Begin to message the vitamins and minerals slowly into the skin from the neck up.

Fourth, take sterile towelettes that have been pre-soaked and cooled in hygroscpic enzymes and place them into the neck and face.

Fifth, take a pre-heated towel and wrap the facial area. The heated towel allows for an increase in capillary action and the face is allowed time to be saturated in the applied solutions.

IV. Oxygenation

This step utilizes an atomizer or nebulizer (sub-micronic delivery system, or SMDS) which should generate sub-micronic particles consistently in the range of 0.5 to 0.9 microns.

Because of the variable ranges of pH changes that the skin has gone through, in the exfoliation process and now with the addition of topical radiant heat the skin has become a more semi-permeable membrane. The skin will now safely absorb a select amount of molecular nutrients on a pore-by-pore basis. More vitamins and minerals are applied for absorption. An example of the solution used in this step and placed in the SMDS for application was prepared as follows:

| Ingredients | Amount |
|---|---|
| purified sea derived trace minerals | 0.001 gm |
| mycelated retinol palmitate | 3 gtts/150 IU |
| mycelated 4-alpha tocopherol | 3 gtts/75 IU |
| simmondsia cheninsis | 3 gtts |
| sterile distilled water | 2.5 ml |
| hypotonic saline | 0.5 ml |

The total amount of solution made is approximately 3 ml.

The procedure for using the oxygenation solution is as follows: First fill the SMDS to a level of 2.5 cc's with the oxygenation solution. Second, add 3 gtts each of mycelated d-alpha tocopherol and mycelated retinol palmitate into the SMDS. Should the user be a smoker, or have parched skin, add 3 gtts of simmondsia cheninsis plus an additional drop of each mycelated vitamin.

Third, close the SMDS and unwrap the heated towels from the facial area. The towelettes may be set aside for use at the end of the treatment. Fourth, turn the oxygen tank to a flow of between 5 and 6 liters/minute and begin oxygenation of the user's skin, from the neck upwards with a depth of approximately ½ inch to 1 inch. Next, make sure the SMDS is upright and at a 45 degree angle. Progressively move the SMDS over the face in small areas so that each pore is oxygenated optimally from a range of 1 inch to 1½ inches.

Continue oxygenation until the whole area is completely saturated. This should require approximately 4 to 5 minutes. When complete, turn the oxygen off and replace the SMDS. Finally, place a few drops of the bacteriostatic cleansing solution onto the towelettes that were taken from the user's face and have the user wipe their hands.

In general, oxygen is responsible for the health and maintenance of every cell in the human body, including skin cells. In today's environment, many factors play a large part in the hindrance of the oxygen molecule to these cells, both externally and internally. Therefore, in today's standard of professional skin care, it has become apparent that the future of skin care must be developed to use oxygen to better serve the millions of people concerned about preventative skin care.

Oxygen is controlled and regulated by various agencies in this country, and as such is classified as a drug. The invention is clinically unique to the field of cosmetology in that, for the first time ever, the professional aesthetician is provided with a strong nutrients base for the care of the skin that will include actual oxygen molecules. The process, as described, allows the skin to respond to and accept moisturized nutrients by an oxygenated mist in a manner not previous set forth in prior art.

It therefore can be seen that the invention accomplishes at least all of its stated objectives.

In the specification there has been set forth a preferred embodiment of the invention, and although specific terms are employed, these are used in a generic and descriptive sense only and not for the purpose of limitation. Changes in the form and the proportion of ingredients as well as in the substitution of equivalents are contemplated as circumstances may suggest or render expedient without departing from the spirit or scope of the invention as further defined in the following claims.

What is claimed is:

1. A method for nutritionally oxygenating an area of skin, said method comprising the steps of:

(a) exfoliating the skin with:

(a') an alkalinic solution consisting of 20–25% almond oil, 0.2–0.5% papin, 28–34% potassium chloride soap, 8–12% aloe vera, 0.3–0.7% bromelain, 0.2–0.5% grapefruit extract, 1–3% isotonic saline, and 32–37% water; and (a") an acidic solution consisting of 5–9% aloe vera, 0.1–0.3% balm mint extract, 0.2–0.5% allantoin, 0.2–0.4% Hawaiian ginger, 0.7–0.9% chamomile, 87–90% water and 2% hypotonic saline;

(b) cleansing the skin with a bacteriostatic solution consisting of 0.2–0.5% of a mixture of wintergreen, spearmint and peppermint oil, 0.2–0.6% citronella, 0.7–1.0% ergocelciserol, 0.1–0.3% balm mint oil extract, 92–97% water and 2.0–4.0% hypotonic saline;

(c) hydrating the skin with an application of vitamins and minerals consisting of 2 drops of 150 I.U. mycelated d-alpha tocopherol, 3 drops of 75 I.U. mycelated retinol palmitate, 2 drops simmondsia cheninsis, 0.4 drops liquid minerals, 0.03 drops hygroscopic enzymes, 30 drops sterile distilled water and 5 drops hypotonic saline; and (d) applying molecular nutrients consisting of 0.001 grams purified trace minerals, 3 drops/150 I.U. mycelated retinol palmitate, 3 drops/75 I.U. mycelated d-alpha tocopherol, 3 drops of simmondsia cheninsis, 2.5 ml sterile distilled water and 0.5 ml hypotonic saline and oxygen gas to the skin using an oxygenating nebulizer.

2. The method of claim 1 wherein the alkaline solution has a pH substantially in the range of 8.2 to 8.5.

3. The method of claim 1 wherein the acidic solution has a pH substantially in the range of 4.3 to 4.5.

4. The method of claim 1 wherein step (a') is applied by massaging the alkalinic solution onto the area of skin.

5. The method of claim 1 wherein step (a") is applied by massaging the acidic solution onto the area of skin.

6. The method of claim 5 wherein step (a") is followed by the step of wiping the topical debris from the area treated.

*7. A method for nutritionally oxygenating an area of skin, said method comprising the step of:*

*applying oxygen to an area of skin at a rate of between 5 to 6 liters/minute at a depth of about ½ inch to 1 inch sufficient to allow the absorption of molecular nutrients selected from the group consisting of mycelated retinol palmitate, mycelated d-alpha tocopherol, and simmondsia cheninsis.*

*8. A method according to claim 7 wherein the oxygen is applied using an atomizer or nebulizer that produces submicronic particles of oxygen.*

*9. A method according to claim 8 wherein the submicronic particles are of a size in the range of 0.5–0.9* microns.

*10. A method according to claim 7 wherein molecular nutrients are applied with the oxygen.*

*11. A method according to claim 7 wherein the oxygen in applied so that each skin pore is oxygenated from a range of 1 inch to 1½ inch.*

*12. A method according to claim 7 wherein the oxygen in applied until the skin area is completely saturated.*

*13. A method according to claim 12 wherein the skin is oxygenated for about 4–5 minutes.*

*14. A method according to claim 7 further including the steps of:*

*exfoliating the skin;*

*cleansing the skin; and*

*hydrating the skin.*

*15. A method according to claim 14 wherein the exfoliation step includes the application of an alkalinic solution and an acidic solution.*

*16. A method according to claim 15 wherein the alkalinic solution has a pH substantially in the range of 8.2–8.5 and the acidic solution has a pH substantially in the range of 4.3–4.5.*

* * * * *